United States Patent
Duncan et al.

(10) Patent No.: US 6,464,997 B1
(45) Date of Patent: Oct. 15, 2002

(54) METHOD OF BIOLOGICAL CONTROL

(75) Inventors: Kelvin Winston Duncan, 27b Lodge Pl., Christchurch (NZ); Angus Ian Macrae, Christchurch (NZ)

(73) Assignee: Kelvin Winston Duncan, Christchurch (NZ)

(*) Notice: Subject to any disclaimer, the term of this patent is extended or adjusted under 35 U.S.C. 154(b) by 0 days.

(21) Appl. No.: 09/319,458

(22) PCT Filed: Dec. 9, 1997

(86) PCT No.: PCT/NZ97/00164

§ 371 (c)(1), (2), (4) Date: Jun. 7, 1999

(87) PCT Pub. No.: WO98/25470

PCT Pub. Date: Jun. 18, 1998

(30) Foreign Application Priority Data

Dec. 9, 1996 (NZ) .................................... 299903
Jan. 31, 1997 (NZ) .................................... 314171

(51) Int. Cl.$^7$ .................................................. A01N 25/32
(52) U.S. Cl. .................... 424/406; 424/405; 424/409; 424/195.17
(58) Field of Search ................. 424/405, 406, 424/409, 417, 420, 195.17; 71/5; 435/254.1, 257.1, 174, 173.8

(56) References Cited

U.S. PATENT DOCUMENTS

| | | | |
|---|---|---|---|
| 4,845,085 A | 7/1989 | Sesin | 514/183 |
| 4,886,756 A | 12/1989 | Kawamura et al. | 435/199 |
| 5,229,118 A | * 7/1993 | Campbell | 424/195.1 |
| 5,585,365 A | 12/1996 | Hayashi et al. | 514/54 |

FOREIGN PATENT DOCUMENTS

| | | |
|---|---|---|
| CN | 1102069 A | 5/1995 |
| CN | 1105566 A | 7/1995 |
| DE | 19646324 A1 | 5/1997 |
| EP | 619112 A1 | 10/1994 |
| EP | 629397 A1 | 12/1994 |
| FR | 2609246 A | 7/1988 |
| JP | 57-36981 | 2/1982 |
| JP | 087294 | 3/1984 |
| JP | 63-63391 | 3/1988 |
| JP | 4320666 | * 11/1992 |
| JP | 107549 | 11/1996 |

OTHER PUBLICATIONS

Mitsuo Takano, Jun–Ichi Sado, Takahira Ogawa, Gyozo Terui, "Freezing and Freeze–Drying of *Spirulina platensis*", MicroBiology, 1973, p. 440–444, vol. 10, Academic Press Inc.

Jorjani, G.H,; Amirani Parvin, "Antibacterial activities of *Spirulina platensis*", *Maj. Iimy Puzshky Danishkadah Jundi Shapur*, 1978, 169142n, vol. 91, (Coll. Med. Technol., Jundi Shapur Univ., Ahvaz, Iran).

Nicolas G. Popovich, "Spirulina", *American Pharmacy*, Jun. 1982, p. 8–10, vol. NS22, No. 6.

Orio Ciferri, Orsola Tiboni, "The Biochemistry and Industrial Potential of *Spirulina* ", *Annual Review of MicroBiology*, 1985, p. 503–526, vol. 39, No. 15.

Suresh P. Thacker, Raman M. Kothari, V. Ramamurthy, "Obtaining Axenica Cultures of Filamentous Cyanobacterium *Spirulina*", *Biotechniques*, 1994, p. 216–217, vol. 16, No. 2.

Kyoko Hayashi, Toshimitsu Hayashi, Ichiro Kojima, "A Natural Suflated Polysaccharide, Calcium Spirulan, Isolated from *Spirulina platensis*: In Vitro and ex Vitro Evaluation of Anti–Herpes Simplex Virus and Anti–Human Immunodeficiency Virus Activities", *AIDS Research and Human Retroviruses*, 1996, p. 1463–1471, vol. 12.

Tohimitsu Hayashi, Koyoko Hayashi, Masaakira Maeda, Ichiro Kojima, "Calcium Spirulan, and Inhibitor of Enveloped Virus Replication, from a Blue–Green Alga *Spirulina platensis*", *Journal of Natural Products*, 1996, p. 83–87, vol. 59.

* cited by examiner

*Primary Examiner*—Neil S. Levy
(74) *Attorney, Agent, or Firm*—Greer, Burns & Crain, Ltd.

(57) ABSTRACT

A method of biological control and inhibit and suppress the growth and effects of fungal contaminants by the use of a treated Spirulina compound includes the steps of preparing the Spirulina compound and applying it to a target site. This site can be a horticultural product, mushroom spawn, an agricultural product or a combination thereof. This method can also be used to inhibit, suppress or remove biological pests where the target site is a fluid containing the pests or a bait station adjacent the source of the pests or along a known flight path of the pests.

9 Claims, No Drawings

METHOD OF BIOLOGICAL CONTROL

TECHNICAL FIELD

The present invention relates to a method of biological control to inhibit and suppress fungal infections or infestations using a treated Spirulina compound as the controlling or inhibiting agent. The present invention further relates to a method of biological control of organisms and animals and more particularly, pests and diseases associated with pests, using a treated Spirulina compound as the controlling or inhibiting agent.

BACKGROUND ART

Spirulina is approved for human and animal consumption as a protein source under international food and drug standards. It also contains carotenoids, vitamins and minerals (Hayashi & Hayashi, "Calcium Spirulan, an Inhibitor of Enveloped Virus Replication, from Blue-Green Alga *Spirulina platensis*", J. Nat Prod (1996), 59, p. 83).

Spirulina have also been found to have anti-viral abilities, as can be seen in the above article and in U.S. Pat. No. 5,585,365 (Hayashi et al). A hot water extract of Spirulina from which a calcium polysaccharide was purified was disclosed. The purified extract was effective for the treatment of viral diseases.

In U.S. Pat. No. 4,845,085 (Sesin) a semi-synthetic compound derived from Nostoc sp. is disclosed as having anti-fungal abilities. However this compound is disclosed as best for only filamentous fungi. Secondary metabolites from species such as Spirulina have also been used as anti-fouling agents (DE19646324 (Abstract)).

In addition Spirulina has been reported as having biological activity for example: to lower blood sugar levels (in diabetes); to lower blood cholesterol; and other effects (Hayashi et al). Other biological activity for Spirulina has been disclosed, for example by Amirani (Chemical Abstracts, 91:169142n); in U.S. Pat. No. 4,886,756 (Kawamura) disclosing a restriction endonuclease from Spirulina; and in J 6303391 (Abstract) a method is disclosed for producing a physiologically active substance from Spirulina.

The use of an agent to hinder the establishment of a competitive organism (pest or contaminant) or to promote the growth of a companion organism is known.

However, at present there is no method of biological control to inhibit and suppress competitive organisms whereby the mutualistic association between the agent and companion organism can be maintained via an external factor without alteration of the agent genotype.

The inventors are not aware of any reports that suggest Spirulina is specifically an antifungal agent (or fungicide) nor that Spirulina can act as an agent for biological control of agricultural and horticultural pests.

It is an object of the present invention to overcome this absence by the use of a treated Spirulina compound. It is a further object of one aspect of the present invention to provide an improved method of biological control whereby the vigour of the agent can be controlled by the exclusion of visible light.

SUMMARY OF THE INVENTION

The present invention provides a method of biological control to inhibit and suppress the growth and effects of fungal contaminants associated with a companion organism (a target partner entering into a mutualistic association with an anti-fungal agent), in which said anti-fungal agent is a treated Spirulina compound, said method including the steps of:

preparation of the treated Spirulina compound; and the application of said compound on or adjacent a target site which site is selected from the group consisting of: horticultural products; mushroom spawn; agricultural products; and a combination thereof; wherein said preparation includes the steps of rehydrating desiccated Spirulina, stressing the culture and freeze drying to a powder.

Preferably, said method further includes a means to control the vigour of said agent, said means being visible light, and wherein said agent is applied as a liquid culture spray.

Advantageously, the intensity of the chlorophyll green colouration of the agent may be used as an indicator of shelf life of a proprietary preparation.

The present invention also provides a method of biological control to inhibit, suppress or remove biological pests wherein a pesticidal agent is used, said agent being a treated Spirulina compound, said method comprising the steps of:

preparation of the treated Spirulina compound; and the application of said compound on or adjacent a target site, said site being selected from the group consisting of: the fluid containing the pests to be suppressed, removed or controlled; and a bait station in or adjacent the source of the pests or along a known flight path of said pests; wherein said preparation includes the steps of rehydrating desiccated Spirulina, stressing the culture and freeze drying to a powder.

Preferably such pests are crustacea and insects, and more particularly, insects regarded as pests in the fields of agriculture, horticulture and medicine. Preferably also the bait station may include a known lure for the pests.

BEST MODE FOR CARRYING OUT THE INVENTION

By way of example only, preferred embodiments of the present invention are described in detail, with reference to a series of Examples.

In the description of the preferred embodiments only, the terms fungal contaminants, companion organisms and agent have the meanings given below:

Fungal contaminants—Deuteromycota and Ascomycota which produce conidia or asci respectively;

Companion Organisms—the target partner entering into a mutualistic association with the agent;

Agent—viable culture of cyanobacterial cells of the genera, Spirulina, possessing both photosynthetic and nitrogen fixation, metabolic activity.

Experiments were carried out using the following

Fungal Contaminants

Hypocreaceae—*Trichoderma viride* Canterbury CTV 1.

The fungal contaminants are available through the Department of Zoology, University of Canterbury, New Zealand.

Companion Organisms—Basidiomycota

One of *Pleurotus pulmonarius* Canterbury CPP 1 (Oyster mushroom); or

*Lentinula edodes* Western Biologicals C 10, C 13 or C 40 (Shiitake mushroom)

The companion organisms were cultivated by standard tissue culture techniques (Staments P, Growing Gourmet & Medicinal Mushrooms, Ten Speed Press, 1995) and are available through the Department of Zoology, University of Canterbury, New Zealand.

Agent: *Spirulina platensis* (Earthrise Farms, Mass Culture Facilities, California).

Compound Preparation

Desiccated *Spirulina platensis* cells were rehydrated in 0.84 w/v sodium bicarbonate (pH 8.5) for approximately 12 hours, preferably under illumination (8–80 Watts/m$^2$).

Optionally, the rehydration solution may further contain 0.04–0.25 w/v sodium sulphide to inhibit bacterial growth.

The culture is stressed by nutrient diminution or partial desiccation to yield a resting stage.

Freeze drying the compound produced an axenic powder. Alternatively, commercially available desiccated *S. platensis* cells (Earthrise Farms) were utilized.

LABORATORY TRIALS

EXAMPLE 1

Companion Organism Infection

*Pleurotus pulmonarius* tissue samples were cultured on PDA plates at 25° C. When the resultant hyphal lawn occupied approximately two thirds of the surface area of the medium, each replicate was streak inoculated with 2.5% *Trichoderma viride* macerated hyphae and spore suspension and incubated for a period of 5–7 days at 25° C. to establish the contaminant to sporulation. Sporulation of the contaminant was visually indicated by the characteristic green colouration of the conidia. The infected plates were subdivided into a control and test series.

Treatment with Agent

The test series was individually surface spray treated with Spirulina platensis compound (0.1%, 1% and 5% w/v).

Whole Plate Comparison

The composition of the test and control microbial populations were qualitatively monitored on a daily basis. The contaminant *T. viride* completely covered the surface area of the control replicate plates within 2–5 days whereas the relative abundance of *T. viride* infection in the test series reduced over time in the presence of the agent, at all tested concentrations (0.1%, 1%, 5% w/v).

Approximately 24 hours after application of the agent, the colouration of the contaminant conidia changed from green to a darker green brown. Within four days, the contaminant conidia had the appearance of a green globular mass and the white hyphae of the *P. pulmonarius* rapidly invaded the green material. After 48 hours of further incubation no trace of the contaminant was visible on the surface of the media and the basidiomycete, *P. pulmonarius* recovered completely to form a continuous lawn on the surface of each test plate.

Light and Scanning Electron Microscopy

Comparative morphological observations of *T. viride* contaminated *P. pulmonarius* cultures were made before and after treatment with the agent. Prior to treatment, the branching pattern of the *T. viride* conidiophores were evident with the phialides differentiating in the characteristic branching structure, terminating in chains of conidia. At one day after treatment the conidia had the appearance of globular structures having little or no surface ornamentation. At day five, the hyphae and conidial structures had coalesced into an amorphous protoplasmic mass which appeared to be unbounded by cell wall *P. pulmonarius* hyphae were observed to be invading the mass. It was concluded that the contaminant was being saprophytically metabolised by the companion organism, *P. pulmonarius*.

The experimental procedure was repeated with the basidiomycete, *L. edodes* and the same sequence of events described above was observed.

EXAMPLE 2

Treatment of Contaminant 2.5% *T. viride* macerated hyphae and spore suspension was streak inoculated on PDA plates and incubated for a period of 5–7 days at 25° C. Upon sporulation, each replicate plate was sprayed with 1% w/v of the agent over 100% or 50% of the medium surface.

Replicates which received 100% spray treatment coverage appeared black within three days of application. The conidiophores and conidia of *T. viride* became is desiccated. No viable spores were produced and no regrowth of the contaminant occurred.

Replicates which received 50% spray treatment coverage showed a discrete boundary differentiation between the area which had and had not been sprayed. The area which had been sprayed deteriorated and turned dark brown or black as observed in the replicates which received 100% spray coverage. However, after a period of approximately five days, the boundary gradually broke down and the agent migrated into the unsprayed area and attacked the previously undamaged contaminant hyphae. The aforesaid observation demonstrated that the agent, like other cyanobacteria, has the ability to move. Cyanobacterial rate of movement has been estimated to be approximately 2.5 mm per day.

EXAMPLE 3

Co-culture Trial

A) Pre-treatment with Agent.

5 g *S. platensis* powder was mixed with commercially available mushroom spawn (*P. pulmonarius* and *L. edodes*). The agent/companion organism mixture was then cultured in 3 kg plastic bags of *Pinus radiata* growth medium in known manner (production bag cultivation). The time to first flush (production of fruiting body or "mushroom"), the morphology of the fruiting bodies and taste were evaluated in comparison to controls.

Treated mushroom spawn showed a 17% increase in growth rate (i.e. 15 days to first flush compared to 18 days) and percentage yield of harvest was 10% above that of the controls. No change in the morphological appearance or taste was detected between that of the fruiting bodies resulting from treated spawn and the controls.

It was deduced from analysis of percentage yield increase and the three day reduction in time to first flush, that the cyanobacterium effects a synergistic interaction with basidiomycete companions. The inventors suggest that the cyanobacterium degrades the chitin component of non-basidiomycete cell walls. However, this proposed mechanism of degradation is yet to be confirmed. Further, the cyanobacterial exudates appear to promote fruiting body production.

B) The Effect of Light Exclusion Upon Treatment Commercially available production bags for the cultivation of edible basidiomycetes develop under suitable environmental conditions in the following sequence. The basidiomycete hyphae grows to form a supportive network wherein the hyphal binding of the growth substrate forms a stable block such that the polythene bag can be removed. The hyphae coat at the surface of the block becomes senescent and is observable as a dense brown mat which is termed 'barking'. Fruiting bodies are produced from the active hyphae beneath the senescent hyphal mat in a plurality of flushes.

Twenty 3 kg *P. pulmonarius* production blocks were spray inoculated with 2.5% w/v *T. viride* macerated hyphae and spore suspension and incubated in an illuminated 25° C. growth room to establish the contaminant to sporulation as hereinbefore described. The contaminated production blocks were subdivided into a control and test series comprising two sets of five replicates. The test series replicates received a surface spray treatment of 1% w/v of the agent.

Both the control and test series replicates were incubated for a further period of approximately three days until sporulation and peripheral hyphal growth of the contaminant *T. viride* was not visible to the naked eye. A first control and test set of replicates were then removed to a completely darkened 25° C. growth room whilst the remaining replicate sets continued to be incubated under illumination. The relative abundance of the respective micro-organisms was monitored on a daily basis.

The control series replicates incubated in the presence or absence of light did not form the characteristic 'barking' senescent hyphae mat around the periphery of the growth substrate. The intensity and distribution of the green colouration of the *T. viride* conidia indicated that the contaminant became dominant or out-competed the basidiomycete within a period of 2–3 days from the date of transference of the first control set to the dark growth room. Investigation of the growth substrate found no actively metabolising *P. pulmonarius* hyphae. The growth substrate of the control series replicates lost the stability of the block structure as the basidiomycete hyphae decayed.

The test series replicates incubated in the presence or absence of light showed a marked decrease in the relative abundance of the contaminant over time. The cessation of *T. viride* sporulation occurred within 4–5 days of treatment. However, the test set incubated in darkness was slower to show clearance of the contaminant hyphae from growth substrate (approximately 2–4 days time lag in comparison to that of the test replicates incubated in the light). The characteristic chlorophyll green colouration of the agent was visible on the blocks and fruiting body production occurred.

The exclusion of light was advantageous in that the virulence of *S. platensis* in causing cell wall degradation of the contaminant increased when vigorous growth of the agent was suppressed by the cessation of photosynthetic metabolism. The companion basidiomycete benefited two fold in that competition for resources with the contaminant and cyanobacterium is kept in check and the damaged contaminant hyphae and probable cyanobacterial exudates resulting from the photosynthesis and nitrogen fixation provide a source of nutrition.

Further, the inventors have found that manipulation of the light intensity of the growth room can affect both the vigour of the agent and the companion organism. Complete darkness switches off the photosynthetic metabolic activity of the agent. The genera Spirulina are photosynthetic, nitrogen-fixing autotrophs and the resultant exudates derived from active cells may provide organic nitrogen and other organically rich nutrients for use by the companion organism.

EXAMPLE 4

In Situ Treatment of Contaminants

*T. viride* Infection of Basidiomycete Fruiting Bodies and Lignocellulosic Substrates.

Commercial cultivations of basidiomycota are prone to spot contaminant fungal infections affecting both the lignocellulosic growth substrates and the mushrooms. The growth rooms provide an ideal aerated and humid environment for the dispersal and growth respectively of fungal contaminants such as *T. viride*.

The inventors have effectively controlled spot infections by spray application of 1% w/v suspension of the agent on to the infected fruiting body tissue. It has been found that spray treatment of infected companion tissue, when the basidiomycete is active, produces a more rapid response. Activation of the companion fungus is effected by watering 2–3 days prior to treatment. Further, shake application of powder has been found to confine and treat minor infections in the growth substrate.

EXAMPLE 5

In Situ Treatment to Control Mosquitoes

Three trials were conducted on a pond of approximately 10 square metres, known to contain mosquito larvae. In each trial, 15 grams of powdered agent (or the dried cream of the above examples) was sprinkled on the surface of the water. All larvae were found dead within one to five days.

The mechanism causing death is unknown except that it results from the larvae consuming the Spirulina. It is suggested that the exo-chitinase digests the peritrophic membrane lining the mid- and hind-gut. This renders the larvae susceptible to death by infective agents.

EXAMPLE 6

Treatment of Flies and Wasps

Ten trials were conducted on wasps and flies by exposing a cream containing 25% v/v of the agent in a commercially greasy base (as a bait) in a area containing flies and wasps in a natural setting. Dead flies and wasps were found in the near vicinity of the bait.

The mechanism is unknown. However it is suggested that a similar mechanism operates causing the death of such insects as the tentative conclusion above under example 5.

While no other insect attractant (or lure) was used in the trials, it will be appreciated that other insect attractants could be added to the bait, without detracting from the efficacy of the cream.

While the invention has been described in respect of a biological control method relating to mushroom cultivation as a preferred embodiment, it will be appreciated that the invention could be used to prevent and treat infection of other fruit and vegetable produce.

What is claimed is:

1. A method of controlling, inhibiting and suppressing the growth of contaminating fungi associated with a mutualistic combination of a *Spirulina platensis* powder functioning as an anti-fungal agent and a fungus selected from the Phylum Basideomycota functioning as a companion organism, said method including the steps of:

preparing the mutualistic combination of said *Spirulina platensis* powder and said fungus selected from the Phylum Basideomnycota; and applying a growth controlling effective amount of said mutualistic combination that includes *Pleurotus pulmonarius* and *Lentinula edodes* on or adjacent a target selected from the group consisting of: horticultural products; Basideomycota growth media; agricultural products; and a combination thereof, said target site containing a contaminating fungus.

2. A method of controlling, inhibiting and suppressing the growth of contaminating fungi as claimed in claim 1 wherein said method is completed under axenic conditions.

3. A method of controlling, inhibiting and suppressing the growth of contaminating fungi as claimed in claim 1 wherein said step of preparing further includes rehydrating said combination with a rehydrating solution containing 0.84 w/v sodium bicarbonate at a pH of 8.5 and the rehydrating is for approximately 12 hours.

4. A method of controlling, inhibiting and suppressing the growth of contaminating fungi as claimed in claim 3 wherein said rehydrating is conducted under illumination at between 8 and 80 Watts/m$^2$.

5. A method of controlling, inhibiting and suppressing the growth of contaminating fungi as claimed in claim 3 wherein the rehydrating solution contains 0.04–0.25 w/v sodium sulphide.

6. A method of controlling, inhibiting and suppressing the growth of contaminating fungi as claimed in claim 1 wherein said method further includes use of visible light to control the rate of growth of the contaminating fungi.

7. A method of controlling, inhibiting and suppressing the growth of contaminating fungi as claimed in claim 2 wherein said method further includes use of visible light to control the rate of growth of the contaminating fungi.

8. A method of controlling, inhibiting and suppressing the growth of contaminating fungi as claimed in claim 1 wherein said mutualistic combination functions as a pesticidal agent.

9. A method of controlling, inhibiting and suppressing the growth of contaminating fungi associated with a mutualistic combination of a *Spirulina platensis* powder functioning as an anti-fungal agent and a fungus selected from the Phylum Basideomycota functioning as a companion organism, said method including the steps of:

preparing the mutualistic combination of said *Spirulina platensis* powder and said fungus selected from the Phylum Basideomycota; and applying a growth controlling effective amount of said mutualistic combination on or adjacent a target selected from the group consisting of:

horticultural products; Basideomycota growth media; agricultural products; and a combination thereof, said target site containing *Trichoderma viride*.

* * * * *